United States Patent [19]

Ukai et al.

[11] Patent Number: 4,939,175

[45] Date of Patent: Jul. 3, 1990

[54] USE OF N,N-DIMETHYL-1-[1-(4-CHLOROPHENYL)-CYCLOBUTYL]-3-METHYLBUTYLAMINE

[75] Inventors: Kiyoharu Ukai, Shiga; Chiharu Masuda, Moriyama; Satoko Kubo, Otsu; Teruo Mukai, Joyo; Terutake Nakagawa, Otsu, all of Japan

[73] Assignee: The Boots Co. PLC, Nottingham, England

[21] Appl. No.: 330,012

[22] Filed: Mar. 29, 1989

[30] Foreign Application Priority Data

Mar. 31, 1988 [JP] Japan ............................. 63-80498

[51] Int. Cl.$^5$ .......................................... A61K 31/135
[52] U.S. Cl. .................................................... 514/646
[58] Field of Search ........................................ 514/646

[56] References Cited

U.S. PATENT DOCUMENTS

| | | | |
|---|---|---|---|
| 4,443,449 | 4/1984 | Jeffery et al. | 424/250 |
| 4,522,828 | 6/1985 | Jeffery et al. | 514/646 |
| 4,746,680 | 5/1988 | Jeffery et al. | 514/646 |
| 4,767,790 | 8/1988 | Jeffery et al. | 514/646 |
| 4,806,570 | 2/1989 | Jeffery et al. | 514/646 |
| 4,814,352 | 3/1989 | Jeffery et al. | 514/646 |
| 4,816,488 | 3/1989 | Rees | 514/646 |
| 4,871,774 | 10/1989 | Rees | 514/646 |

FOREIGN PATENT DOCUMENTS 2098602A 11/1982 United Kingdom.
2184122A 6/1987 United Kingdom.

OTHER PUBLICATIONS

Chem. Abst. 109 (1988)-204745a.
Buckett et al., "Prog. Nuero-Psychopharmacol. & Biol. Psychiat", *The Pharmacology of Sibutramine Hydrochloride*, 1988, vol. 12, pp. 575-584.
Luscombe, et al., "British Journal of Pharmaceology", vol. 92, Dec. 1987, Sep. 9-11, 1987.
Buckett, et al., "British Journal of Pharmaceology", vol. 90, Mar. 1987, Dec. 17-19, 1986.

*Primary Examiner*—Stanley J. Friedman
*Attorney, Agent, or Firm*—Armstrong, Nikaido, Marmelstein, Kubovcik & Murray

[57] ABSTRACT

Use of N,N-dimethyl-1-[1-(4-chlorophenyl)cyclobutyl]-3-methylbutylamine or a pharmacologically acceptable acid addition salt thereof for manufacture of a cerebral function improver for the treatment of cerebral function disorders, which is useful as an improver for cerebral function disorders such as amnestic syndrome, senile dementia and Parkinson's disease, since it can intensively activate the central nervous system, especially dopamine neuron, and also increase the spontaneous movement in human or animal.

5 Claims, 1 Drawing Sheet

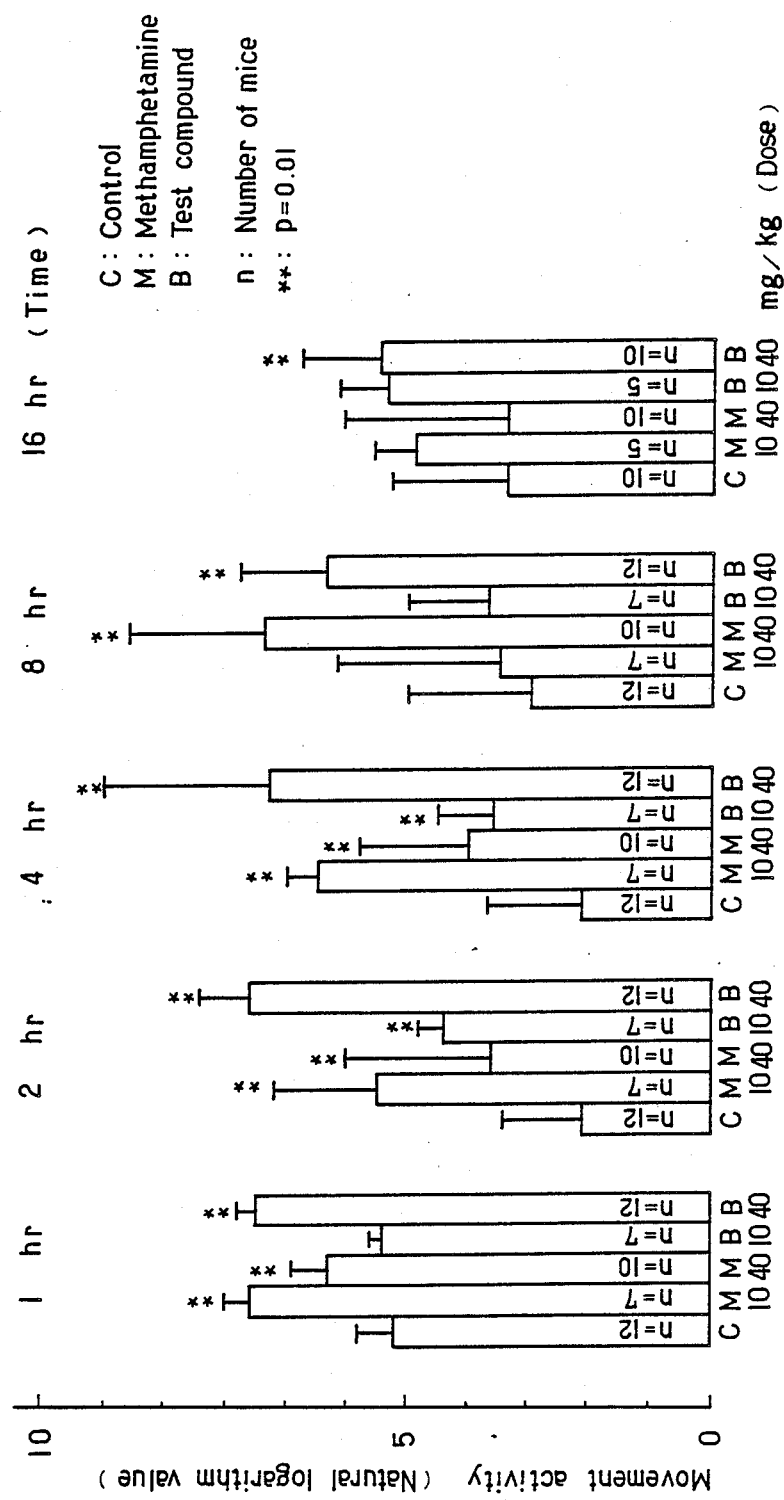

USE OF N,N-DIMETHYL-1-[1-(4-CHLOROPHENYL)CYCLOBUTYL]-3-METHYLBUTYLAMINE

BACKGROUND OF THE INVENTION

The present invention relates to a use of N,N-dimethyl-1-[1-(4-chlorophenyl)cyclobutyl]-3-methylbutylamine or pharmacologically acceptable acid addition salt thereof for manufacture of a cerebral function improver in the treatment of cerebral function disorders.

It is described that N,N-dimethyl-1-[1-(4-chlorophenyl)cyclobutyl]-3-methylbutylamine has a therapeutical effect as an antidepressant in the Japanese Unexamined Patent Publication No. 181,043 (1982).

In recent years, cerebral function disorders has caused public discussion in attendance on the shift to the high-aged society. The cerebral function disorders are induced by cerebrovascular diseases such as cerebral infarction, cerebral bleeding, cerebral arteriosclerosis, cerebral venous thrombosis, head injuries and the like and give a variety of symptoms as secondary diseases, for example, disturbance of consciousness, senile dementia, coma, lowering of attention, speech disorder and the like. Therefore, there are desired a drug having a high activity with little side effect for the treatment of the cerebral function disorders.

It has now been found that the above compound is especially useful for manufacture of a cerebral function improver in the treatment of cerebral function disorders, wherein intelectural functions in brain make lowered, such as amnestic syndrome, senile dementia and Parkinson's disease since the compound has surprisingly an intensive effect on memory and learning in preclinical studies. Accordingly, this invention has been accomplished.

SUMMARY OF THE INVENTION

In accordance with the present invention, there is provided use of N,N-dimethyl-1-[1-(4-chlorophenyl)cyclobutyl]-3-methylbutylamine or a pharmacologically acceptable acid addition salt thereof for manufacture of a cerebral function improver for the treatment of cerebral function disorders.

BRIEF DESCRIPTION OF THE DRAWINGS

FIG. 1 is a graph showing the effect of the test samples on spontaneous movement in mice.

DETAILED DESCRIPTION

The compound according to the present invention may be used as a free base or an acid addition salt thereof. In the latter case, it is preferable to be in the form of pharmacologically acceptable salts, for instance, hydrochloride, sulfate, tartrate, succinate and acidic amino acid salts such as aspartate and glutamate.

The daily dosage of the cerebral function improver of the present invention to adults is preferably in the range of from 2 to 50 mg. Examples of the dosage form are, for instance, tablet, capsule, powder, granule, liquid preparation, parenteral injection and the like.

Moreover, if necessary, pharmacologically acceptable additives such as stabilizer, surface active agent preserver and flavor may be used to prepare the cerebral function improver of the present invention.

The cerebral function improver having the compound as an active ingredient may be suitably used for the treatment of symptons such as amnestic syndrome, disturbance of consciousness, senile dementia, coma, lowering of attention, speech disorder and the like, which are induced by the lower or disorder of cerebral function, since the compound has such an effect as activating the central nervous system through an intensive activation of dopamine neuron in addition to both norepinephrine and serotonin neuron.

Moreover, the cerebral function improver of the present invention can be used in the treatment of Parkinson's disease, Lennox syndrome, autism, hyperkinetic syndrome, schizophrenia and the like, based on the increase of spontaneous movement and the enhancing effect of dopamine activity.

The present invention is more specifically described and explained by means of the following Test Examples and Formulation Examples in which N,N-dimethyl-1-[1-(4-chlorophenyl)cyclobutyl]3-methylbutylamine hydrochloride is used as the test compound.

It is to be understood that the present invention is not limited to the following Examples, and various changes and modifications may be made in the invention without departing from the spirit and scope thereof.

TEST EXAMPLE 1

Action of the test samples on the memory defect artificially induced by electroconvulsive shock in mice C 57 BL/6 male mice (5 week age) weighing of $19\pm2$ g were fed for a week under the conditions of 22° to 24° C. and about 60% R.H., and subjected to the test. The test was carried out by using a box divided into two rooms (light and dark). The dark room (23.5 cm in height, 12 cm in width and 24 cm in length) was surrounded by black inner walls and provided with a stainless steel bar on the floor to give the mouse an electric shock. The light room (triangular in shape with 15 cm in height, 13 cm in bottom side length and 12 cm in oblique-side length) was surrounded by transparent walls except for the partition wall, provided with a guillotine door (5 cm in height and 3 cm in width) at the center of the partition wall, and illuminated with a 100 Watt electric bulb at a position of 50 cm above the floor.

The test was carried out according to the procedures as follows:

(1) Taming trial

After the mouse was put in the light room, the guillotine door was opened. When the limbs of the mouse entered into the dark room, the door was closed. After keeping the mouse for 10 seconds in the dark room, it was brought back to the home cage.

(2) Acquisition trial

The mouse was put in the light room at the time of 30 minutes after the taming trial, and then the guillotine door was opened. When the limbs of the mouse entered into the dark room, the door was closed and 0.4 mA of electric shock was applied to the limbs of the mouse for 3 seconds. Then, the mouse was brought back to the home cage.

(3) Testing trial

The mouse was put in the light room at the time of 24 hours after the acquisition trial, and then the guillotine door was opened. The time, which was taken for the limbs of the mouse to enter into the dark room, was measured up to 300 seconds as a scale of the reaction latency and the number of mice which did not enter into the dark room during testing trial, i.e. showing latency longer than 300 seconds, was counted.

(4) Preparation for mice with memory defect induced by electroconvulsive shocks

Electroconvulsive shock (30 mA, 0.5 second) was applied to the mouse at its ears immediately after the acquisition trial, which caused tetany on the mouse. The mice, which survived after the righting reflex had disappeared, were subjected to the testing trial 24 hours later.

(5) Drug administration

The test compound was dissolved in distilled water, and the solution was orally administered, in a dose shown in Table 1 to each group consisting of 10 heads at the time of one hour before the testing trial.

(6) Amnestic syndrome

The testing trial (3) was conducted at one hour after the test compound administration, and the reaction latency was examined for each test mouse. The obtained results are shown in Table 1, and Amnestic syndrome rate (%) is expressed as follows:

$$\text{Amnestic syndrome rate (\%)} = \frac{A - B}{A} \times 100$$

A: Number of mice tested
B: Number of mice showing latency longer than 300 seconds

TABLE 1

| Test sample | Dose of the test sample (mg/kg) | ECS | Number of mice | Number of mice showing latency longer than 300 seconds | Amnestic syndrome rate (%) |
|---|---|---|---|---|---|
| Control (Distilled water) | | − | 10 | 6 | 40 |
| Control (Distilled water) | | + | 10 | 2 | 80 |
| Test compound | 0.3 | + | 10 | 4 | 60 |
| | 1.0 | + | 10 | 3 | 70 |
| | 3.0 | + | 10 | 7 | 30 |
| | 10.0 | + | 10 | 9 | 10 |

ECS: Electroconvulsive shock

TEST EXAMPLE 2

Effect of the test samples on the inhibition of conditioned avoidance response induced by reserpine in rats Std-Wistar male rats (8 to 9 week age) weighing of 270 to 300 g were fed under the conditions of 23±2° C., 60±10% R.H. and artificial lighting from 7 AM to 7 PM for a week, and then subjected to the test.

The test was carried out by using a shuttle box. The shuttle box used herein was a rectangular box, which was equipped with a buzzer for conditioned stimulus at the upper part and grids of 2 mm in diameter, for non-conditioned stimulus, at intervals of 1 cm on the floor, and divided into two equal sized compartments by a hurdle of 5 cm in height.

The schedule for inducing the conditioned avoidance response was controlled by a computer, and all the observed results of avoidance or escape response were recorded automatically.

The avoidance condition was carried out as follows:

After the conditioned stimulus of the buzzer with sound signal for 5 seconds, the non-conditioned stimulus of the foot shock was given for 5 seconds to rats. Each stimulus was stopped immediately, if the rat jumped over the hurdle to the other compartment during the conditioned or non-conditioned stimulus. The rats were trained for 50 times a day at the intervals of 30 to 40 seconds, then the rats, which showed 80% and more of the conditioned avoidance response, were used for the next experiment.

The above-mentioned rats were put on the trials for 25 times. Then the rats were given reserpine (1 mg/kg, intraperitoneally). The rats were tested for 15 times at the time of 18 to 20 hours after the reserpine administration, and then they were divided into several groups (6 mice/group).

The test sample was dissolved in distilled water and administered orally to each group at 24 to 26 hours after the reserpine administration. For reference, distilled water as control sample, and amitriptyline and amantadine as test drugs were used.

At one hour after the test sample administration, the rats were put on the trials for 25 times and the conditioned avoidance responce was compared between the control group (distilled water administration), the test compound-administered group and the test drug-administered groups.

The obtained results are shown in Table 2.

TABLE 2

| | | Conditioned avoidance response (%) | | |
|---|---|---|---|---|
| Test sample | Dose of the test sample (mg/kg) | before administration of reserpine | 18 to 20 hours after administration of reserpine | 1 hour after administration of the test sample |
| Control (Distilled water) | | 93 | 1 | 2 |
| Test compound | 10 | 90 | 2 | 82 |
| Amitriptyline | 10 | 93 | 1 | 1 |
| Amitriptyline | 40 | 94 | 7 | 0 |
| Amantadine | 10 | 94 | 3 | 2 |
| Amantadine | 50 | 95 | 3 | 38 |

*reserpine dose: 1 mg/kg

TEST EXAMPLE 3

Effect of the test samples on the depletion of dopamine induced by 1-methyl-4-phenyl-1,2,3,6-tetrahydropyrolidine (hereinafter referred to as MPTP) in mice whole brain The test sample, wherein dosulepin, amitriptyline, imipramine, desipramine, mianserin, maprotiline, clomipramine and methamphetamine were used as test drugs in Experiment I, amantadine and methamphetamine in Experiment II and also sufoxazine, indeloxazine and methamphetamine in Experiment III, was administered orally to SlC: ddy strain male mice (7 to 10 heads/group) and after 30 minutes, 50 mg/kg of MPTP was injected subcutaneously. Distilled water in Experiment I, II and III, and a 5% Gum Acacia solution in Experiment III were used as control sample. For reference, the drugs shown in the Table 3 are used.

After one week, the mice were decapitated. The whole brain was rapidly removd and homogenized in 0.06M perchloric acid with 3,4-dihydroxybenzyl amine as an internal standard. The homogenate was centrifuged and then, dopamine in the supernatant was determined by means of high performance liquid chromatograpy with electrochemical detection.

The obtained results are shown in Table 3.

TABLE 3

| Test sample | Dose of the test sample (mg/kg) | Percentage of the amount of dopamine in the treated group against the amount of dopamine in the non-treated group (%) |
|---|---|---|
| Experiment I | | |
| Non-treatment | | 100 ± 10 |
| Control | | 71 ± 11 |
| Test compound | 10 | 83 ± 12* |
| | 30 | 85 ± 6* |
| Dosulepin | 10 | 70 ± 13 |
| | 30 | 77 ± 12 |
| Amitriptyline | 10 | 81 ± 15 |
| | 30 | 77 ± 15 |
| Imipramine | 10 | 80 ± 14 |
| | 30 | 73 ± 14 |
| Desipramine | 10 | 74 ± 15 |
| | 30 | 79 ± 18 |
| Mianserin | 10 | 72 ± 16 |
| | 30 | 69 ± 8 |
| Maprotiline | 10 | 65 ± 17 |
| | 30 | 74 ± 17 |
| Clomipramine | 10 | 74 ± 13 |
| | 30 | 74 ± 14 |
| Methamphetamine | 3 | 97 ± 14** |
| Experiment II | | |
| Non-treatment | | 100 ± 21 |
| Control | | 88 ± 20 |
| Test compound | 10 | 111 ± 8* |
| Amantadine | 10 | 77 ± 21 |
| | 30 | 64 ± 16 |
| Methamphetamine | 3 | 102 ± 21* |
| Experiment III | | |
| Non-treatment | | 100 ± 9 |
| Control | | 67 ± 12 |
| Control (5% of Gum Acacia) | | 72 ± 16 |
| Sufoxazine | 10 | 76 ± 17 |
| | 30 | 68 ± 14 |
| Indeloxazine | 10 | 77 ± 17 |
| | 30 | 72 ± 19 |
| Methamphetamine | 3 | 91 ± 20** |

*P < 0.05
**P < 0.01

TEST EXAMPLE 4

Effect of the test samples on the re-uptake of $^3$H-dopamine in vitro $P_2$ fraction was prepared from the whole brain of Std: Wistar strain male rat. For reference, amitriptyline was used in Experiment I and dosulepin, imipramine and maprotiline were used in Experiment II. $^3$H-dopamine was added in the synaptosome suspension which had been prepared from the $P_2$ fraction. The obtained mixture was incubated at 37° C. for 20 minutes and then subjected to the suction filtration with Whatman GF/B filter paper.

The obtained filter paper was put in a vial containing 10 ml of toluene type scintillator and its radioactivity was measured by means of liquid scintillation counter. The amount of the specific re-uptake of $^3$H-dopamine was obtained by subtracting the amount of re-uptake at 0° C. as blank.

The obtained results are shown in Table 4.

TABLE 4

| Test sample | Number of mice | IC50 ($\mu$M) |
|---|---|---|
| Experiment I | | |
| Test compound | 6 | 2.0 |
| Amitriptyline | 6 | 7.7 |
| Experiment II | | |
| Amitriptyline | 6 | 8.2 |
| Dosulepin | 6 | 9.6 |
| Imipramine | 6 | 15.0 |
| Maprotiline | 6 | 13.0 |

TEST EXAMPLE 5

Effect of the test samples on the depletion of norepinephrine induced by 6-hydroxydopamine in rat heart.

The test sample was administered orally to Std: Wistar male rats and after 30 minutes, 6-hydroxydopamine (20 mg/kg) was injected intraperitoneally.

At 16 hours after injection of 6-hydroxydopamine, the rats were killed. The whole heart was rapidly removed and homogenized in 0.05M perchloric acid with isoproterenol (10 mg/ml) as an internal standard. The homogenate was centrifuged and then the amount of norepinephrine in the supernatant was determined by means of high performance liquid chromatography with electrochemical detection.

Desipramine was used as the reference drug and distilled water was used as control sample.

The obtained results are shown in Table 5.

TABLE 5

| Test sample | Dose of the test sample (mg/kg) | Amount of Norepinephrine (ng/g) |
|---|---|---|
| Non-treatment | | 425 ± 49 |
| Control | | 20 ± 4 |
| Test compound | 0.625 | 169 ± 34** |
| | 1.25 | 247 ± 49** |
| | 2.5 | 306 ± 27** |
| Desipramine | 0.625 | 35 ± 4 |
| | 1.25 | 74 ± 26 |
| | 2.5 | 211 ± 79** |

**p < 0.01

TEST EXAMPLE 6

Effect of the test samples on the depletion of serotonin (hereinafter referred to as "5-HT") induced by p-chloroamphetamine The test sample was administered orally to SlC:ddy made mice and after 60 minutes, p-chloroamphetamine (10 mg/kg) was injected intraperitoneally.

At 6 hours later, the mice were decapitated. The whole brain was rapidly removed and homogenized in 0.06M perchloric acid with N-methylserotonin (10 $\mu$g/ml) as an internal standard. The homogenate was centrifuged and then the amount of 5-HT in the supernatant was determined by high performance liquid chromatography with electrochemical detection.

Amitriptyline was used as the reference drug and distilled water was used as control sample.

The obtained results are shown in Table 6.

TABLE 6

| Test sample | Dose of the test sample (mg/kg) | Percentages of the amount of 5-HT in the treated group against the amount of 5-HT in the non-treated group (%) |
|---|---|---|
| Non-treatment | | 100 ± 10 |
| Control | | 48 ± 6 |
| Test compound | 3 | 64 ± 8** |
| | 10 | 103 ± 10** |
| Amitriptyline | 10 | 50 ± 4 |
| | 30 | 56 ± 10** |
| | 90 | 92 ± 8** |

**$p < 0.01$

TEST EXAMPLE 7

Effect of the test samples on circling behavior in rats with unilateral substantia nigra lesions Std: Wistar male rats (8 heads/group) were used. The rat with unilateral substantia nigra lesions was made by injecting 8 μg/4 μl of 6-hydroxydopamine to the right side of substantia nigra.

The test sample was administered orally to the rat. At 2 hours later, the number of circling behavior per 10 minutes was counted.

Amantadine was used as the reference drug and distilled water was used as control sample.

The obtained results are shown in Table 7.

TABLE 7

| Test sample | Dose of the test sample (mg/kg) | Number of circling behavior per 10 min. |
|---|---|---|
| Control | | 0.1 ± 0.4 |
| Test compound | 3 | 3.0 ± 2.9** |
| | 10 | 5.1 ± 4.4** |
| Amantadine | 50 | 0.4 ± 0.7 |

**$p < 0.01$

TEST EXAMPLE 8

Effect of the test samples on the sleeping time induced by thiopental

The test sample was administered orally to Std: Wistar male rats, and at 60 minutes later, sodium thiopental (40 mg/kg) was injected intravenously.

The duration of sleeping time was determined as the time period between the injection of thiopental and return of the righting reflex.

Distilled water was used as control sample.

The obtained results are shown in Table 8.

TABLE 8

| Test sample | Dose (mg/kg) | Sleeping time (sec) |
|---|---|---|
| Control | | 500.8 ± 12.0 |
| Test compound | 10 | 345.6 ± 82.2** |
| | 30 | 338.5 ± 43.7** |

**$p < 0.01$

TEST EXAMPLE 9

Effect of the test samples on the sponteneous movement of mice

The test sample was administered orally to SIC:ddy male mice. Immediately after, the amount of movement activity of the test mice was measured for 16 hours, at the time of 1, 2, 4, 8 and 16 hours respectively after the oral administration, by means of spontaneous movement measuring system (displacement measuring type).

Methamphetamine was used as the reference drug and distilled water was used as control sample.

The obtained results are shown in FIG. 1, columns and bars represent the mean±S.D. and statistical significance was evaluated by the multiple comparison test of Dunnet's type.

TEST EXAMPLE 10

Acute toxicity

SIC:ddy male mice (10 heads/group) were used.

After the oral administration of the test smaple, desipramine was used as the test drug, to the mice, the number of the dead mice was counted at 0.5, 1, 2, 4, 18 and 24 hours respectively after the oral administration.

The obtained results are shown in Table 9.

TABLE 9

| Test sample | Dose of the test sample (mg/kg) | Number of dead mice per 10 mice Time (hr) | | | | | |
|---|---|---|---|---|---|---|---|
| | | 0.5 | 1 | 2 | 4 | 18 | 24 |
| Test compound | 200 | 0 | 1 | 1 | 1 | 2 | 2 |
| | 800 | 4 | 5 | 5 | 6 | 9 | 9 |
| Desipramine | 200 | 0 | 0 | 0 | 0 | 0 | 0 |
| | 800 | 10 | 10 | 10 | 10 | 10 | 10 |

The cerebral function improvers of the present invention containing the test compound as an active ingredient were prepared according to the following Formulation Examples.

FORMULATION EXAMPLE 1

(Tablets)

The tablets (150 mg/one tablet) were prepared according to the prescription as follows:

| Component | Content (mg) |
|---|---|
| Test compound | 10 |
| Corn starch | 134 |
| Hydroxypropylcellulose | 4 |
| Magnesium stearate | 2 |

FORMULATION EXAMPLE 2

(Capsules)

The capsules (No. 5) were produced by filled with the 100 mg of base materials, which were prepared according the following prescription.

| Component | Content (mg) |
|---|---|
| Test compound | 10 |
| Lactose | 50 |
| Corn starch | 30 |
| Crystalline cellulose | 8 |
| Magnesium stearate | 2 |

FORMULATION EXAMPLE 3

(Injections)

The injections were prepared by dissolving 10 mg of the test compound in 1 ml of physiological salt solution, followed by adjusting the pH of the obtained solution to 7.4.

In addition to the ingredients or components used in the Examples, other ingredients or components can be used in the Examples as set forth in the specification to obtain substantially the same results.

What we claim is:

1. A method of treating an amnestic syndrome condition or a senile dementia condition in a patient having at least one of said conditions, said method comprising administering to the patient a therapeutically effective amount of N,N-dimethyl-1-[1-(4-chlorophenyl)-cyclobutyl]-3-methylbutylamine or a pharmacologically acceptable acid addition salt thereof.

2. Method of claim 1, wherein said patient has amnestic syndrome, and the therapeutically amount of said compound is an amnestic syndrome treating-effective amount.

3. Method of claim 2, wherein said amount is 20 to 50 mg per day for an adult.

4. Method of claim 1, wherein said patient has senile dementia, and said effective amount is a senile dementia treating-effective amount.

5. Method of claim 4, wherein said amount is from 2 to 50 mg per day for an adult.

* * * * *